(12) United States Patent
Takikawa et al.

(10) Patent No.: US 12,048,501 B2
(45) Date of Patent: Jul. 30, 2024

(54) MEDICAL IMAGE DIAGNOSIS APPARATUS, SURGERY ASSISTANCE ROBOT APPARATUS, SURGERY ASSISTANCE ROBOT CONTROLLING APPARATUS, AND CONTROLLING METHOD

(71) Applicant: CANON MEDICAL SYSTEMS CORPORATION, Otawara (JP)

(72) Inventors: Sayaka Takikawa, Nasushiobara (JP); Takayuki Kojima, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 517 days.

(21) Appl. No.: 16/838,422

(22) Filed: Apr. 2, 2020

(65) Prior Publication Data

US 2020/0315724 A1 Oct. 8, 2020

(30) Foreign Application Priority Data

Apr. 3, 2019 (JP) .................................. 2019-071075
Feb. 27, 2020 (JP) .................................. 2020-031543

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/10* (2016.02); *A61B 34/20* (2016.02); *A61B 34/25* (2016.02);
(Continued)

(58) Field of Classification Search
CPC ......... A61B 34/37; A61B 34/10; A61B 34/20; A61B 34/25; A61B 34/35
See application file for complete search history.

(56) References Cited

U.S. PATENT DOCUMENTS 8,010,180 B2 * 8/2011 Quaid .................... A61B 34/71
600/426
11,058,498 B2 * 7/2021 Shelton, IV ........... G16H 20/30
(Continued)

FOREIGN PATENT DOCUMENTS

JP 2003-299674 A 10/2003
JP 2005-21353 A 1/2005
(Continued)

OTHER PUBLICATIONS

Japanese Office Action issued on Jul. 4, 2023 in the corresponding Japanese Patent Application No. 2020-031543, 3 pages.
(Continued)

*Primary Examiner* — Baisakhi Roy
(74) *Attorney, Agent, or Firm* — Oblon, McClelland, Maier & Neustadt, L.L.P.

(57) ABSTRACT

A medical image diagnosis apparatus according to an embodiment includes processing circuitry. The processing circuitry is configured to obtain operation information used for putting a surgery assistance robot into motion, the surgery assistance robot holding a medical tool to be inserted into the body of a subject and being configured to move the medical tool. The processing circuitry is configured to estimate the position of the medical tool with respect to a surrounding site expected after the medical tool is moved, on the basis of a positional relationship between the medical tool inside the body of the subject and the surrounding site as well as the operation information and is configured to control the motion of the surgery assistance robot on the basis of a result of the estimation.

13 Claims, 6 Drawing Sheets

(51) Int. Cl.
  *A61B 34/10* (2016.01)
  *A61B 34/20* (2016.01)
  *A61B 34/35* (2016.01)
(52) U.S. Cl.
  CPC ........ *A61B 34/35* (2016.02); *A61B 2034/102* (2016.02); *A61B 2034/107* (2016.02); *A61B 2034/2055* (2016.02); *A61B 2034/2065* (2016.02)

(56) References Cited

U.S. PATENT DOCUMENTS

| | | | |
|---|---|---|---|
| 11,311,348 B2* | 4/2022 | Simi | A61B 90/06 |
| 2012/0165652 A1* | 6/2012 | Dempsey | A61N 5/1067 |
| | | | 600/410 |
| 2014/0330108 A1 | 11/2014 | Dempsey | |
| 2019/0159845 A1 | 5/2019 | Dempsey | |
| 2019/0254761 A1* | 8/2019 | Sen | B25J 15/0019 |
| 2019/0336226 A1* | 11/2019 | Raines | A61B 34/76 |
| 2020/0138544 A1* | 5/2020 | Bono | B60B 19/12 |
| 2020/0188046 A1* | 6/2020 | Overmyer | A61B 34/20 |
| 2020/0315724 A1* | 10/2020 | Takikawa | A61B 34/10 |

FOREIGN PATENT DOCUMENTS

| | | |
|---|---|---|
| JP | 2005-324038 A | 11/2005 |
| JP | 2006-312079 A | 11/2006 |
| JP | 2006-320427 A | 11/2006 |
| JP | 2008-538184 A | 10/2008 |
| JP | 4171833 B2 | 10/2008 |
| JP | 2010-69006 A | 4/2010 |
| JP | 2015-521084 A | 7/2015 |
| JP | 2016-518148 A | 6/2016 |
| JP | 2017-60782 A | 3/2017 |
| JP | 2018-134151 A | 8/2018 |
| JP | 2018-529442 A | 10/2018 |
| WO | WO 2013/181503 A1 | 12/2013 |
| WO | WO 2014/139021 A1 | 9/2014 |

OTHER PUBLICATIONS

Japanese Office Action issued on Sep. 19, 2023 in Japanese Patent Application No. 2020-031543, 3 pages.

* cited by examiner

FIG.4
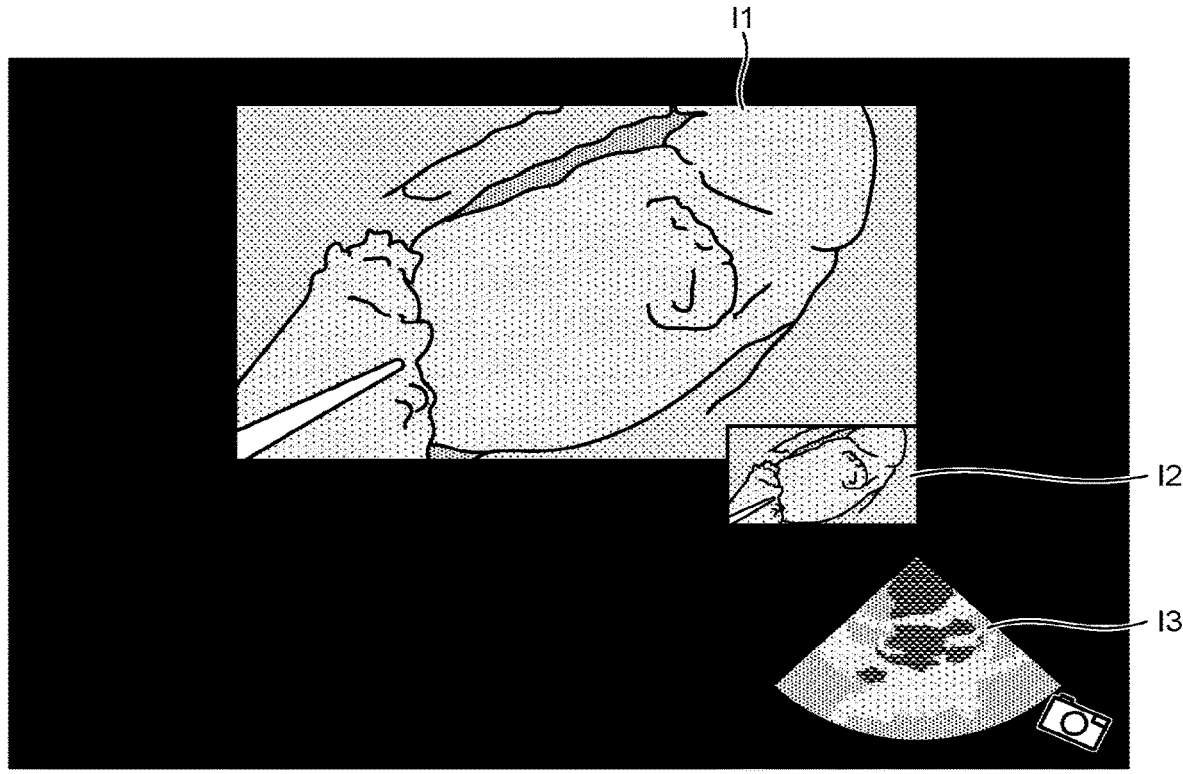
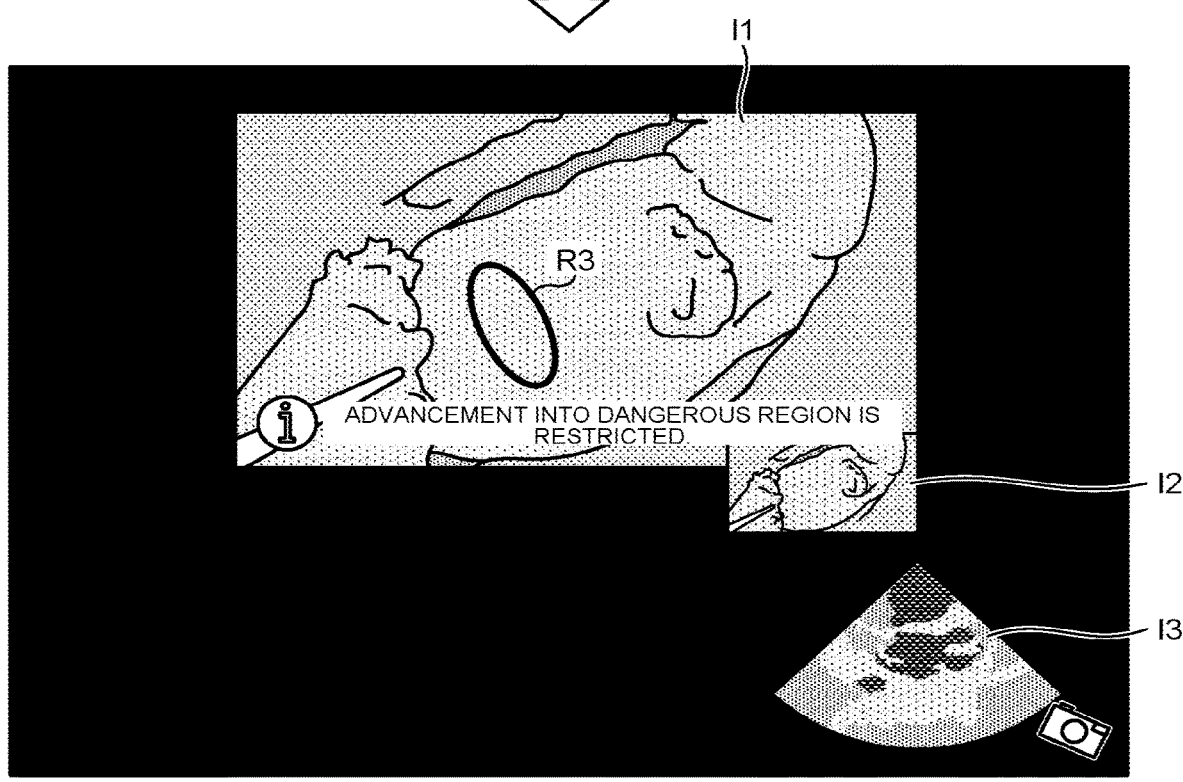

MEDICAL IMAGE DIAGNOSIS APPARATUS, SURGERY ASSISTANCE ROBOT APPARATUS, SURGERY ASSISTANCE ROBOT CONTROLLING APPARATUS, AND CONTROLLING METHOD

CROSS-REFERENCE TO RELATED APPLICATIONS

This application is based upon and claims the benefit of priority from Japanese Patent Application No. 2019-71075, filed on Apr. 3, 2019 and Japanese Patent Application No. 2020-031543, filed on Feb. 27, 2020; the entire contents of which are incorporated herein by reference.

FIELD

Embodiments described herein relate generally to a medical image diagnosis apparatus, a surgery assistance robot apparatus, a surgery assistance robot controlling apparatus, and a controlling method.

BACKGROUND

Surgery assistance robot apparatus have conventionally been used in surgery. A surgery assistance robot apparatus is configured to reproduce hand movements of the practitioner as movements of the distal ends of forceps in a real-time manner and thus makes it possible to perform surgery precisely. For example, because laparoscopic surgery performed by using this type of surgery assistance robot apparatus is less invasive than laparotomy surgery, there are benefits such as a quicker recovery after the surgery, a shorter hospitalization time period, less pain after the surgery, and a smaller amount of blood transfusion required during the surgery.

BRIEF DESCRIPTION OF THE DRAWINGS

FIG. 4 is a drawing illustrating examples of display control realized by a controlling function according to the first embodiment;

DETAILED DESCRIPTION

According to an embodiment, a medical image diagnosis apparatus includes processing circuitry. The processing circuitry is configured to obtain operation information used for putting a surgery assistance robot into motion, the surgery assistance robot holding a medical tool to be inserted into a body of a subject and being configured to move the medical tool. The processing circuitry is configured to estimate a position of the medical tool with respect to a surrounding site expected after the medical tool is moved, on a basis of a positional relationship between the medical tool inside the body of the subject and the surrounding site as well as the operation information. The processing circuitry is configured to control the motion of the surgery assistance robot on a basis of a result of the estimation.

Exemplary embodiments of a medical image diagnosis apparatus, a surgery assistance robot apparatus, a surgery assistance robot controlling apparatus, and a controlling program will be explained in detail below, with reference to the accompanying drawings. In the following embodiments, the surgery assistance robot controlling apparatus will be explained as an example. Further, possible embodiments of the medical image diagnosis apparatus, the surgery assistance robot apparatus, the surgery assistance robot controlling apparatus, and the controlling program of the present disclosure are not limited to the embodiments described below. Further, it is possible to combine each of the embodiments with any other embodiment or with conventional techniques, as long as no conflict occurs in the processing.

First Embodiment

Figure 1:
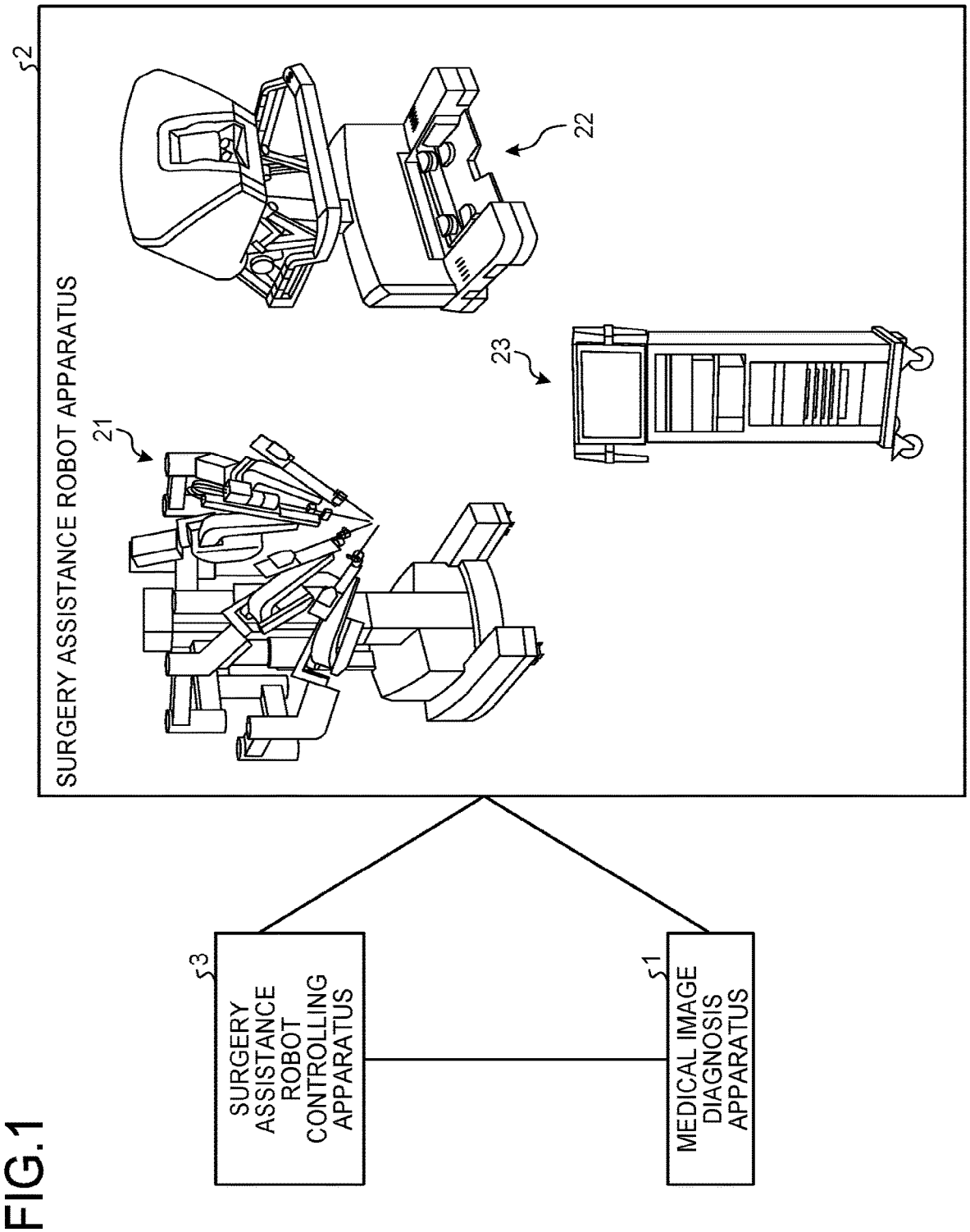
FIG. 1 is a drawing illustrating an exemplary configuration of a surgery assistance robot system according to a first embodiment.

FIG. 1 is a drawing illustrating an exemplary configuration of a surgery assistance robot system according to a first embodiment. As illustrated in FIG. 1, the surgery assistance robot system according to the first embodiment includes a medical image diagnosis apparatus 1, a surgery assistance robot apparatus 2, and a surgery assistance robot controlling apparatus 3. In the present example, the apparatuses are communicably connected to one another via a network constructed in a wired or wireless manner.

The medical image diagnosis apparatus 1 is an X-ray diagnosis apparatus, an X-ray Computed Tomography (CT) apparatus, a Magnetic Resonance Imaging (MRI) apparatus, an ultrasound diagnosis apparatus, a Single Photon-Emission Computed Tomography (SPECT)-CT apparatus in which a SPECT apparatus and an X-ray CT apparatus are integrally formed, a Positron Emission Tomography (PET)-CT apparatus in which a PET apparatus and an X-ray CT apparatus are integrally formed, or a group of apparatuses including any of these apparatuses. Further, the medical image diagnosis apparatus 1 according to the first embodiment is capable of acquiring three-dimensional medical image data (volume data).

In this situation, the medical image diagnosis apparatus 1 is configured to acquire three-dimensional medical image data during surgery using the surgery assistance robot apparatus 2 and to transmit the acquired three-dimensional medical image data to the surgery assistance robot apparatus 2 and to the surgery assistance robot controlling apparatus 3. Further, the medical image diagnosis apparatus 1 is also capable of transmitting results of various types of analyses performed on the acquired medical image data, to the surgery assistance robot apparatus 2 and to the surgery assistance robot controlling apparatus 3.

As illustrated in FIG. 1, for example, the surgery assistance robot apparatus 2 includes a robot arm 21, a console 22, and a display controlling apparatus 23. For example, the surgery assistance robot apparatus 2 is configured to provide surgery assistance by reproducing an operation received by the console 22 as movements of arms and forceps of the robot arm 21 in a real-time manner.

The robot arm 21 includes the plurality of arms holding medical tools such as forceps, an endoscope, and the like, as well as one or more driving mechanisms for putting the arms and the distal ends of the forceps into motion. Each of the arms is configured to move a medical tool held on the distal end side thereof to a desired position, as a result of a plurality of movable parts moving in accordance with an operation received by the console 22, the movable parts being provided with the driving mechanism such as a motor, an actuator, or the like. Further, the forceps held by any of the arms is configured to carry out various manipulations, as a result of a plurality of movable parts moving in accordance with an operation received by the console 22.

In the present example, the forceps held by any of the arms are available in various shapes that can realize various functions such as gripping, peeling, and severing. During surgery, forceps may be replaced as appropriate according to purposes. By using the various types of forces, a practitioner is able to carry out manipulations using the forceps such as, for example, pinching a tissue, cutting a tissue, raking out a cut tissue, sewing a tissue while holding a needle with the forces, and the like, by operating the console 22. Further, for example, forceps having functions of an electric scalpel used for stopping bleeding may be held by any of the arms.

Further, although the movements of the arms and the forceps are able to accurately reproduce operations performed by the practitioner, it is also possible to apply various corrections thereto. For example, the arms and the forceps are able to reproduce certain motion after a correction is made on unstable hand movements of the practitioner. Further, the arms and the forceps are able to reproduce certain motion having a moving amount corrected from an operation amount by which the practitioner actually operates an operation interface. In one example, it is possible to control the arms and the forceps to perform the motion having a moving amount twice (or half) as large as an operation amount by which the practitioner actually performs an operation, without changing the moving direction thereof. Also, it is possible to set the correction of the moving amount with various magnitudes, besides twice as large and half as large.

As explained above, the robot arm 21 has the movable parts in the arms and in the forceps. Because the movable parts are configured to perform the motion in a wide range and in a fine-tuned manner and because the various types of correcting processes are applied thereto, it is to realize a movable range and a precision level equivalent to or better than the human arms and hands.

Further, any one of the arms of the robot arm 21 is able to hold an endoscope used for imaging a surgical region. Similarly to the arms described above, the arm holding the endoscope is also configured to move the endoscope to a position corresponding to an operation performed by an operator, as a result of a plurality of movable parts moving in accordance with the operation received by the console 22, the movable parts being provided with a driving mechanism such as a motor, an actuator, or the like.

Further, any one of the arms of the robot arm 21 is also able to hold a medical tool such as an ultrasound probe. Similarly to the arms described above, the arm holding the ultrasound probe is also configured to move the ultrasound probe to a position corresponding to an operation performed by the operator, as a result of a plurality of movable parts moving in accordance with the operation received by the console 22, the movable parts being provided with a drive mechanism such as a motor, an actuator, or the like. In this situation, the ultrasound probe is configured to scan a range (e.g., inside of an organ) that cannot be visualized by the endoscope.

The console 22 includes the operation interface for operating the arms of the robot arm 21, the forceps, the endoscope, the ultrasound probe, and the like, as well as a display for displaying pictures imaged by the endoscope, and a button, a switch, a foot switch, and the like having various functions. For example, the practitioner performs surgery by operating the arms of the robot arm 21, the forceps, the endoscope, and/or the like, by operating the operation interface while viewing the picture displayed on the display, while sitting down facing the console 22.

In this situation, the operation interface of the console 22 is gripped by the operator and is configured to receive movements of the human arm and fingers and to immediately transfer the movements to the robot arm 21 accurately. As a result, the forceps or the endoscope inserted in the abdominal cavity or the thoracic cavity of a subject perform the same motion. For example, the tips of the forces open and close in accordance with the opening/closing motion of the thumb and the index finger of the practitioner gripping the operation interface. As a result, operations such as pinching and stabilizing a tissue, peeling a tissue, and the like performed.

The display controlling apparatus 23 is configured to exercise various control related to displaying images during the surgery. More specifically, the display controlling apparatus 23 receives images from the endoscope or the medical image diagnosis apparatus 1, performs various types of processes such as an image quality adjustment, and exercises control so that a display thereof or the display included in the console 22 displays the images. For example, the display controlling apparatus 23 is able to enable other doctors and nurses besides the practitioner to understand how the surgery is carried out in a real-time manner, by causing the display thereof to display the same images as the images displayed on the display of the console 22.

The surgery assistance robot controlling apparatus 3 is configured to judge a contact state with a surrounding site, on the basis of three-dimensional medical image data received from the medical image diagnosis apparatus 1 and operation information received from the surgery assistance robot apparatus 2 and to control motion of the robot arm in accordance with a judgment result. More specifically, the surgery assistance robot controlling apparatus 3 judges the contact state of a medical tool with the surrounding site expected when the robot arm is controlled in accordance with the operation information, on the basis of a positional relationship at the current point in time between the three-dimensional medical image data and the medical tool held by the robot arm as well as the operation information and further controls the motion of the robot arm in accordance with the judgment result.

For example, during manipulations using the surgery assistance robot apparatus 2, there is a possibility that unexpected bleeding or a damage in another organ may occur during the surgery. Thus, the practitioner is required to have certain skills to perform the manipulations safely and effectively. When unexpected bleeding or a damage in an organ should occur, it is necessary to switch the procedure to laparotomy immediately; however, because various tools are attached to the subject, it may be difficult in some situations to quickly switch the surgery procedure. To cope with these situations, the surgery assistance robot controlling apparatus 3 according to the present embodiment is configured to judge, in advance through a simulation, the contact state of the medical tool with the surrounding site expected when the robot arm is controlled in accordance with the operation information and to control the robot arm according to the operation information, provided that safety is confirmed. It is therefore possible to improve safety of the manipulations using the surgery assistance robot apparatus 2.

Figure 2:
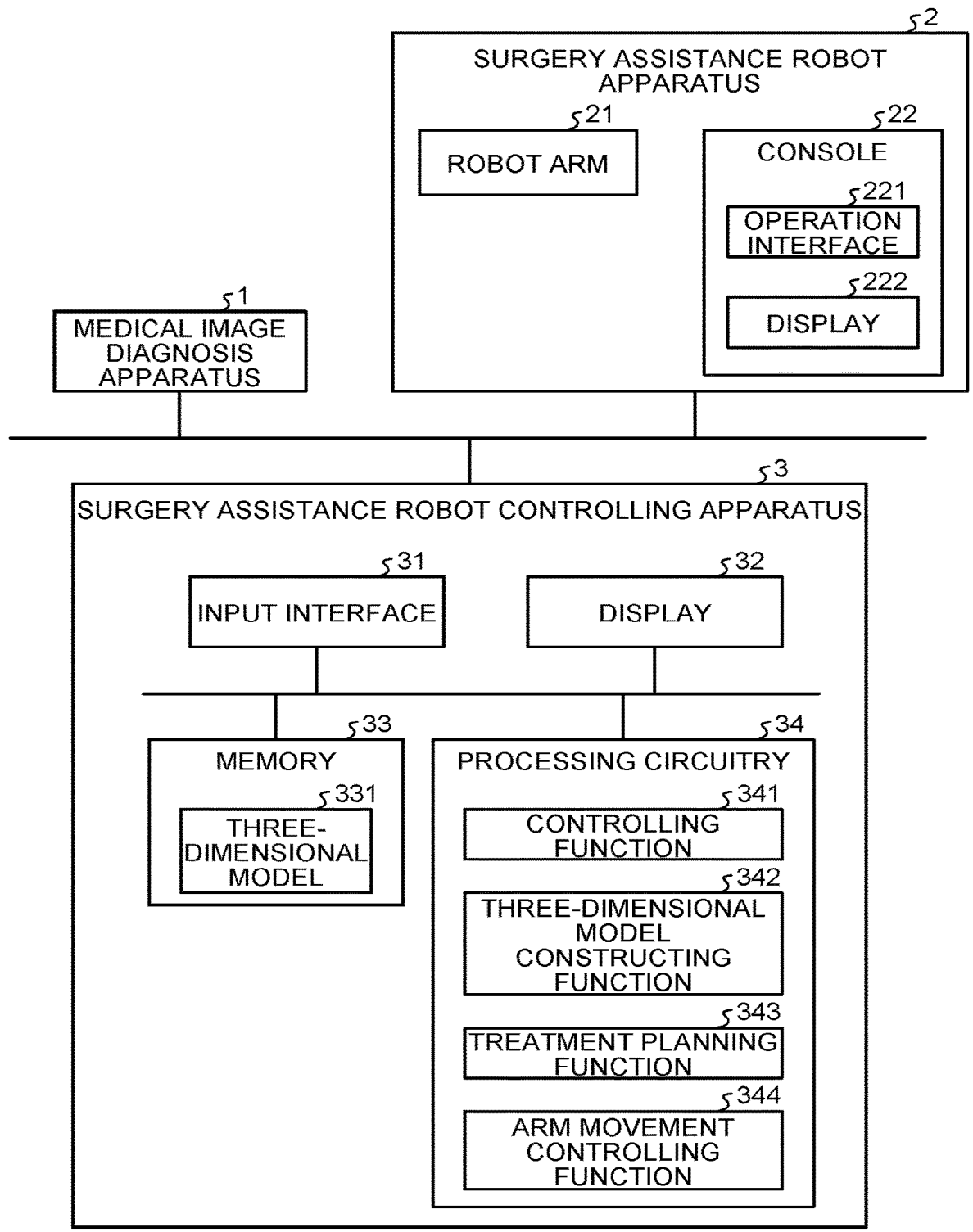
FIG. 2 is a diagram illustrating an exemplary configuration of a surgery assistance robot controlling apparatus according to the first embodiment.

Next, a configuration of the surgery assistance robot controlling apparatus 3 will be explained. FIG. 2 is a diagram illustrating an exemplary configuration of the surgery assistance robot controlling apparatus 3 according to the first embodiment. As illustrated in FIG. 2, the surgery assistance robot controlling apparatus 3 includes an input interface 31, a display 32, a memory 33, and processing circuitry 34. For example, the surgery assistance robot controlling apparatus 3 is realized by using a computer apparatus such as a workstation.

Although not illustrated, the medical image diagnosis apparatus 1, the surgery assistance robot apparatus 2, and the surgery assistance robot controlling apparatus 3 each have a communication interface. Further, the medical image diagnosis apparatus 1, the surgery assistance robot apparatus 2, and the surgery assistance robot controlling apparatus 3 are connected via the communication interfaces and the network, so as to transmit and receive various types of data. Each of the communication interfaces may be realized by using, for example, a network card, a network adaptor, a Network Interface Controller (NIC), or the like.

The input interface 31 is connected to the processing circuitry 34 and is configured to receive input operations of various types of instructions and information from an operator. More specifically, the input interface 31 is configured to convert the input operations received from the operator into electric signals and to output the electric signals to the processing circuitry 34. For example, the input interface 31 is realized by using a trackball, a switch button, a mouse, a keyboard, a touchpad on which input operations are performed by touching the operation surface thereof, a touch screen in which a display screen and a touchpad are integrally formed, a contactless input circuit using an optical sensor, an audio input circuit, and/or the like. In the present disclosure, the input interface 31 does not necessarily have to include physical operation component parts such as a mouse, a keyboard, and/or the like. Possible examples of the input interface 31 include an electric signal processing circuitry configured to receive an electric signal corresponding to an input operation from an external input device provided separately from the device and to output the received electric signal to a controlling circuitry.

The display 32 is connected to the processing circuitry 34 and is configured to display various types of information and images. More specifically, the display 32 is configured to convert data of the information and the images sent thereto from the processing circuitry 34 into display-purpose electric signals and to output the display-purpose electric signals. For example, the display 32 is realized by using a liquid crystal monitor, a Cathode Ray Tube (CRT) monitor, a touch panel, or the like.

The memory 33 is connected to the processing circuitry 34 and is configured to store therein various types of data. For example, the memory 33 is configured to store therein medical image data received from the medical image diagnosis apparatus 1 and the operation information received from the surgery assistance robot apparatus 2. Further, the memory 33 is configured to store therein design information including the shapes and the sizes of medical tools (e.g., various types of forceps, endoscopes, and ultrasound probes) used by the surgery assistance robot apparatus 2 and arrangement states observed when the medical tools are held by the robot arm 21 (coordinate information indicating positional relationships between each of the medical tools and the arm).

Further, the memory 33 is configured to store therein information indicating a positional relationship between a medical tool inside the body of the subject (hereinafter, "subject's body") and a surrounding site. More specifically, the memory 33 is configured to store therein coordinate information indicating the relative positional relationship between the medical tool inside the subject's body and the surrounding site of the medical tool. In this situation, the surrounding site is another region or organ different from the region or organ subject to a manipulation. In one example, the surrounding site may be a blood vessel or a location that should not be damaged. For example, as illustrated in FIG. 2, the memory 33 is configured to store therein a three-dimensional model 331 indicating a relative positional relationship between a medical tool inside the subject's body and a surrounding site of the medical tool. Details of the three-dimensional model 331 will be explained later.

Further, the memory 33 is configured to store therein various types of programs that realize various types of functions when being read and executed by the processing circuitry 34. For example, the memory 33 is realized by using a semiconductor memory element such as a Random Access Memory (RAM) or a flash memory, or a hard disk, an optical disk, or the like.

The processing circuitry 34 is configured to control motion of the surgery assistance robot controlling apparatus 3 in accordance with the input operations received from the operator via the input interface 31. For example, the processing circuitry 34 is realized by using a processor.

The processing circuitry 34 is configured to execute a controlling function 341, a three-dimensional model constructing function 342, a treatment planning function 343, and an arm movement controlling function 344. In this situation, the controlling function 341 is an example of an obtaining unit and a display controlling unit. The three-dimensional model constructing function 342 is an example of a generating unit. The treatment planning function 343 and the arm movement controlling function 344 are each an example of a controlling unit.

The controlling function 341 is configured to exercise control so that processes are performed in accordance with various types of requests input via the input interface 31. For example, the controlling function 341 is configured to control the transmission and reception of the medical image data, the operation information, the design information, and the like performed via the communication interface, the storing of information into the memory 33, and the display of information (e.g., images and processing results) on the display 32.

For example, the controlling function 341 is configured to obtain the three-dimensional medical image data from the medical image diagnosis apparatus 1. Further, the controlling function 341 is configured to obtain the operation information indicating an operation performed by the practitioner on an operation interface 221 of the console 22 included in the surgery assistance robot apparatus 2. In one example, the controlling function 341 obtains information about moving amounts of an arm and a medical tool corresponding to movements of the fingers of the practitioner. In this situation, the controlling function 341 obtains the information about the moving amount obtained by applying the correcting process to the movements of the practitioner. In other words, the controlling function 341 obtains the information about the moving amounts of the arm and the medical tool resulting from the process of correcting unstable hand movements and moving amounts applied to the movements of the fingers and the like of the practitioner.

Further, the controlling function 341 is configured to exercise control so as to present the control exercised by the arm movement controlling function 344 (explained later) to the practitioner or the like. More specifically, the controlling function 341 is configured to exercise control so as to present control information indicating what type of control is exercised by the arm movement controlling function 344 on the robot arm and the medical tool, to the practitioner or the like. Details of this function will be explained later.

The three-dimensional model constructing function 342 is configured to generate the information indicating the positional relationship between the medical tool inside the subject's body and the surrounding site and to store the generated information into the memory 33. More specifically, the three-dimensional model constructing function 342 is configured to generate the coordinate information indicating the relative positional relationship between the medical tool inside the subject's body and the surrounding site of the medical tool and to store the generated coordinate information into the memory 33. For example, on the basis of the three-dimensional medical image data and the design information obtained by the controlling function 341, the three-dimensional model constructing function 342 is configured to generate the three-dimensional model 331 indicating the relative positional relationship between the medical tool inside the subject's body and the surrounding site of the medical tool and to store the generated three-dimensional model 331 into the memory 33.

Figure 3:
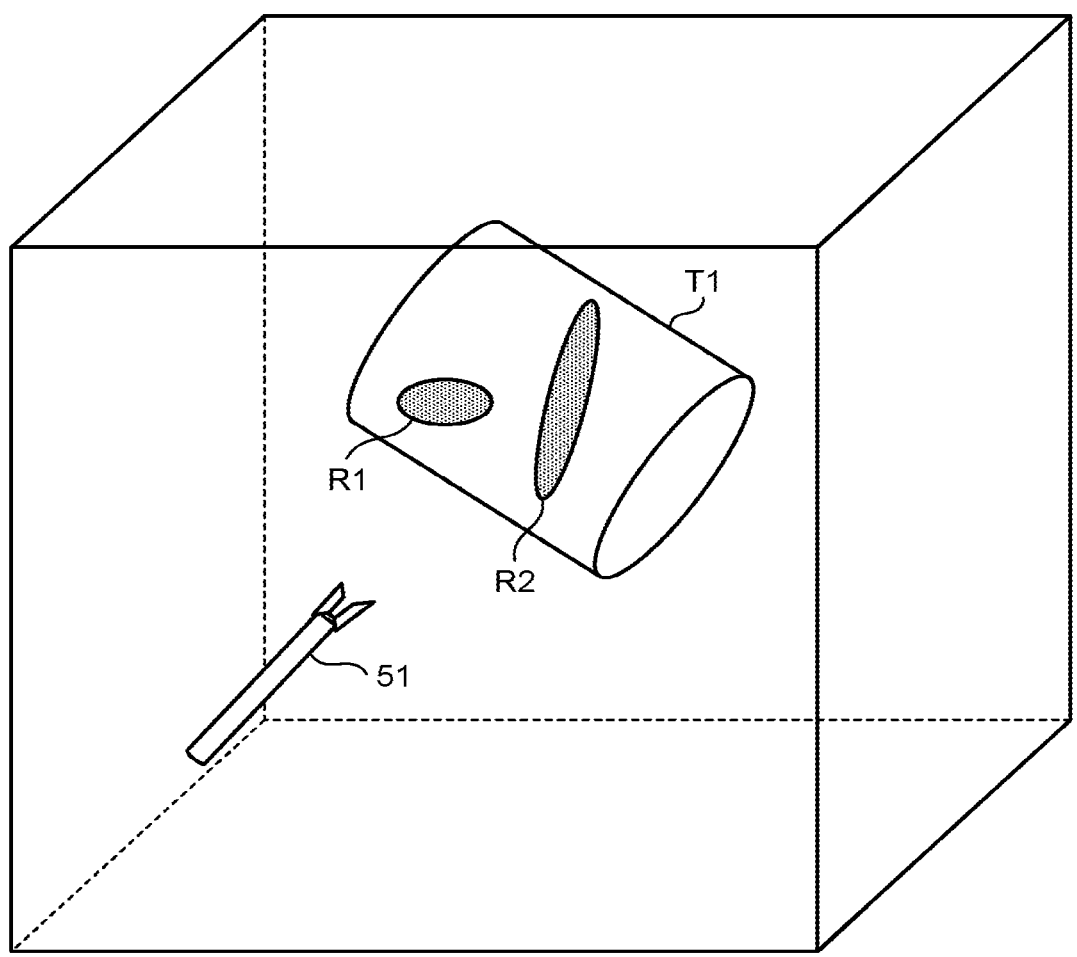
FIG. 3 is a schematic drawing of a three-dimensional model according to the first embodiment.

FIG. 3 is a schematic drawing of the three-dimensional model 331 according to the first embodiment. For example, the three-dimensional model constructing function 342 is configured to generate the three-dimensional model 331 indicating a positional relationship between forceps 51 and a tissue T1 as illustrated in FIG. 3, on the basis of the three-dimensional medical image data and the design information. In this situation, the three-dimensional model constructing function 342 is configured to generate the three-dimensional model 331 by using various methods depending on how the medical image data was acquired.

For example, when an ultrasound probe is held on one of the arms of the robot arm 21, so that an ultrasound diagnosis apparatus serving as the medical image diagnosis apparatus 1 acquires three-dimensional ultrasound image data, the three-dimensional model constructing function 342 generates the three-dimensional model 331, by applying the tissue in the three-dimensional ultrasound image data to the arrangement state (the coordinate information) included in the design information. In other words, when an ultrasound probe is held by an arm, it is possible to specify the position of the ultrasound probe in the coordinate system of the robot arm 21, on the basis of the arrangement state of the ultrasound probe with respect to the arm and the design information of the ultrasound probe. For this reason, it is not necessary to perform a position aligning process on the coordinate system of the robot arm 21 and the coordinate system of the ultrasound diagnosis apparatus.

Accordingly, the three-dimensional model constructing function 342 specifies the position of the ultrasound probe in the coordinate system of the robot arm 21, on the basis of the current arrangement state of the robot arm 21. Further, the three-dimensional model constructing function 342 arranges the ultrasound image data in the coordinate system of the robot arm 21, by arranging the obtained three-dimensional ultrasound image data to fit the specified position of the ultrasound probe. For example, the three-dimensional model constructing function 342 arranges the ultrasound image data in the position of the transmission and reception surface of the ultrasound probe. As a result, the three-dimensional model constructing function 342 is able to obtain the coordinate information indicating a relative positional relationship between the forceps 51 held by another arm of the robot arm 21 and the tissue T1 in the ultrasound image data.

Further, on the basis of the obtained coordinate information, the three-dimensional model constructing function 342 generates the three-dimensional model 331 as illustrated in FIG. 3 in which a model indicating the three-dimensional structure of the forceps 51 and a model indicating the three-dimensional structure of the tissue T1 are arranged in the three-dimensional coordinate system.

In another example, when the three-dimensional medical image data is acquired by the medical image diagnosis apparatus 1 represented by an X-ray diagnosis apparatus or an X-ray CT apparatus, the three-dimensional model constructing function 342 is configured to generate the three-dimensional model 331 on the basis of a positional relationship between the forceps 51 and the tissue T1 in the acquired medical image data. In other words, when the three-dimensional image data is acquired by using an X-ray diagnosis apparatus or an X-ray CT apparatus, a medical tool inserted in the subject's body is imaged together with the tissue inside the subject's body.

Accordingly, the three-dimensional model constructing function 342 obtains coordinate information indicating the relative positional relationship between the forceps 51 and the tissue T1, by extracting, from the obtained three-dimensional medical image data, a region corresponding to the forceps 51 and another region corresponding to the tissue T1. Further, on the basis of the obtained coordinate information, the three-dimensional model constructing function 342 generates the three-dimensional model 331 as illustrated in FIG. 3 in which the model indicating the three-dimensional structure of the forceps 51 and the model indicating the three-dimensional structure of the tissue T1 are arranged in the three-dimensional coordinate system. To extract these regions, it is possible to use any of existing methods as appropriate, such as a method using an anatomical feature point (an anatomical landmark) or a region expansion method based on CT values.

In yet another example, when three-dimensional ultrasound image data is acquired by using a peroral ultrasound probe or through an ultrasound probe scan performed by another medical doctor different from the practitioner, the three-dimensional model constructing function 342 at first performs a position aligning process between the coordinate system of the ultrasound image data and the coordinate system of the robot arm 21. For example, the three-dimensional model constructing function 342 performs the position aligning process between the coordinate system of the ultrasound image data and the coordinate system of the robot arm 21, by performing a position aligning process on the positions of feature points included in the ultrasound image data and the positions of corresponding feature points included in the coordinate system of the robot arm 21.

In one example, the three-dimensional model constructing function 342 extracts the surface of a characteristic tissue (e.g., the surface of a predetermined organ) from the ultrasound image data. Further, the three-dimensional model constructing function 342 extracts the surface of the corresponding tissue from a picture taken by an endoscope. After that, the three-dimensional model constructing function 342 performs a position aligning process while assuming the surface of the tissue extracted from the ultrasound image data to be the same position as the surface of the tissue extracted from the picture taken by the endoscope. Because the endoscope is held by one of the arms of the robot arm 21, the three-dimensional model constructing function 342 is able to specify the position of the endoscope in the coordinate system of the robot arm 21, on the basis of the arrangement state included in the design information.

Accordingly, the three-dimensional model constructing function 342 is able to specify the coordinates of the surface of the tissue in the coordinate system of the robot arm 21, by performing the position aligning process on the surface of the tissue extracted from the ultrasound image data and the surface of the tissue extracted from the picture taken by the endoscope. Further, by arranging the surface of the tissue extracted from the ultrasound image data at the specified coordinates, the three-dimensional model constructing function 342 arranges the ultrasound image data in the coordinate system of the robot arm 21.

As a result, the three-dimensional model constructing function 342 is able to obtain the coordinate information indicating the relative positional relationship between the forceps 51 held by another one of the arms of the robot arm 21 and the tissue T1 in the ultrasound image data. Further, on the basis of the obtained coordinate information, the three-dimensional model constructing function 342 generates the three-dimensional model 331 as illustrated in FIG. 3 in which the model indicating the three-dimensional structure of the forceps 51 and the model indicating the three-dimensional of the tissue T1 are arranged in the three-dimensional coordinate system.

In the example above, the feature points are used for the position aligning process between the coordinate system of the ultrasound image data and the coordinate system of the robot arm 21; however, it is possible to use, as appropriate, any existing applicable position aligning process for the position aligning process between the coordinate system of the ultrasound image data and the coordinate system of the robot arm 21. For example, it is also acceptable to attach a position sensor to the ultrasound probe operated by a medical doctor, so as to perform a position aligning process between the coordinate system of ultrasound image data and the coordinate system of the robot arm 21, by using coordinate information of the position sensor.

As explained above, the three-dimensional model constructing function 342 is able to generate the three-dimensional model 331 by using the various methods. In this situation, the three-dimensional model constructing function 342 is configured to generate the three-dimensional model 331 at various timing during the manipulation using the surgery assistance robot apparatus 2.

For example, during the manipulation using the surgery assistance robot apparatus 2, medical image data is at first acquired before the surgery, so as to make a treatment plan by using the acquired medical image data. Accordingly, the three-dimensional model constructing function 342 at first generates the three-dimensional model 331 of the inside of the subject's body, by using the medical image data acquired before the surgery. In this situation, the three-dimensional model 331 generated by using the medical image data acquired before the surgery includes only the tissue T1 illustrated in FIG. 3, for example, because the medical tool has not yet been inserted in the subject's body.

Further, during the surgery, the three-dimensional model constructing function 342 corrects the three-dimensional model 331, when the structure inside the subject's body has changed and when the position of the medical tool inside the subject's body has changed. For example, the three-dimensional model constructing function 342 corrects the three-dimensional model 331 at least at each of the times when the posture of the subject is fixed, when a space is formed in the abdominal cavity, and before and after a site is removed, during the surgery.

For example, when total prostatectomy is performed by using the surgery assistance robot apparatus 2, a manipulation is performed while the subject is in the posture where the head is kept lower, for the purpose of keeping the intestines in the abdominal cavity away from the prostate. In other words, by arranging the subject in the posture where the head is kept lower, the intestines are brought down toward the head and kept away from the prostate, so as to create a better field of view for the surroundings of the prostate. As explained herein, when the posture of the subject changes before the manipulation is started, the shape of the three-dimensional model 331 generated before the surgery is different from the actual shape of the inside of the abdominal cavity. To cope with this situation, the three-dimensional model constructing function 342 corrects the stored three-dimensional model 331 by re-generating a three-dimensional model 331 when the posture of the subject is fixed at the start of the manipulation.

As another example, when surgery is performed inside the abdominal cavity by using the surgery assistance robot apparatus 2, a space is formed in the abdominal cavity for the purpose of creating the space where a medical tool can move around in the abdominal cavity. For example, the space may be formed in the abdominal cavity by filling the abdominal cavity with carbon dioxide, or the space may be formed in the abdominal cavity by lifting the abdominal wall. This is an important procedure for ensuring a sufficient space in the abdominal cavity to perform the manipulation safely. It should be noted that, however, when the space is formed in the abdominal cavity, the shape of the three-dimensional model 331 generated before the surgery is different from the actual shape of the inside of the abdominal cavity. To cope with this situation, the three-dimensional model constructing function 342 corrects the stored three-dimensional model 331, by re-generating a three-dimensional model 331 when the space is formed in the abdominal cavity at the start of the surgery.

As yet another example, during a manipulation using the surgery assistance robot apparatus 2, the shape inside the abdominal cavity may change in some situations, as a result of a site being removed. For example, when total prostatectomy is performed, the shape of the inside of the abdominal cavity significantly changes between before and after the removal of the prostate. To cope with this situation, the three-dimensional model constructing function 342 generates the three-dimensional model 331 at the time when the site is removed during the manipulation. In this situation, the three-dimensional model constructing function 342 is also capable of storing three-dimensional models 331 before and after the removal of the site into the memory 33. In other words, the three-dimensional model constructing function 342 stores the three-dimensional model before the site removal and the three-dimensional model after the site removal into the memory 33. In that situation, for example, it is possible to evaluate the manipulation regarding the site removal, by using the two stored three-dimensional models.

Further, for example, the three-dimensional model constructing function 342 is also capable of correcting the stored three-dimensional model 331 by re-generating a three-dimensional model 331, every time the medical tool in the abdominal cavity moves during the surgery.

As explained above, the three-dimensional model constructing function 342 generates the three-dimensional model 331 with various timing. In relation to this, it is possible to make a treatment plan and to designate a surrounding site, by using the three-dimensional models generated by the three-dimensional model constructing function 342. For example, the controlling function 341 causes the display 32 to display the three-dimensional model illustrated in FIG. 3. Via the input interface 31, the operator designates a region R1 subject to treatment and a region R2 indicating a blood vessel or a region that should not be damaged, with respect to the tissue T1.

In this situation, the regions designated by the operator are marked in the three-dimensional model, so that position information thereof is stored in the memory 33. In this situation, the designation of the surrounding site does not necessarily have to be performed by the operator and may automatically be performed. For example, the blood vessel and organ of the tissue T1 may be extracted by automatic segmentation so as to be automatically set as the region R2. Further, although FIG. 3 illustrates the example in which only the region R2 representing a blood vessel or a region that should not be damaged is set as the surrounding site, possible embodiments are not limited to this example. It is also acceptable to automatically set the region other than the region R1 that is subject to the treatment and was designated by the operator, as a surrounding site.

Returning to the description of FIG. 2, the treatment planning function 343 makes a treatment plan on the basis of the position of the region subject to the treatment. For example, the treatment planning function 343 determines an approach path of the medica tool, on the basis of the position of the region R1 in FIG. 3 and the shapes of the surroundings. In one example, the treatment planning function 343 determines the approach path of the medical tool (e.g., coordinate information in the passing) to the region R1, on the basis of the coordinates of the region R1 being set, the coordinates of the surrounding site, and other factors such as the shape of the surroundings. After that, the treatment planning function 343 stores the determined treatment plan into the memory 33. Every time the three-dimensional model is corrected, the treatment planning function 343 corrects the treatment plan.

On the basis of the positional relationship between the medical tool inside the subject's body and the surrounding site as well as the operation information, the arm movement controlling function 344 is configured to estimate the position of the medical tool with respect to the surrounding site expected after the medical tool is moved and to further control motion of the surgery assistance robot apparatus 2 on the basis of a result of the estimation. More specifically, the arm movement controlling function 344 is configured to estimate the contact state between the surrounding site and the medical tool expected after the medical tool is moved and to control the motion of the surgery assistance robot apparatus 2 on the basis of the result of the estimation. In other words, the arm movement controlling function 344 is configured to simulate how the medical tool will be moved by the operation performed by the practitioner and to control the motion of the surgery assistance robot apparatus 2 in accordance with a result of the simulation.

In this situation, for example, the arm movement controlling function 344 obtains the positional relationship on the basis of the three-dimensional model indicating the medical tool and the site inside the subject's body. In other words, the arm movement controlling function 344 obtains the information about the positional relationship between the medical tool inside the subject's body and the surrounding site, by reading the three-dimensional model 331 stored in the memory 33. In this situation, every time the three-dimensional model 331 is corrected, the arm movement controlling function 344 reads the three-dimensional model 331 from the memory 33. In other words, the arm movement controlling function 344 obtains a positional relationship at least at each of the times when the posture of the subject is fixed, when a space is formed in the abdominal cavity, and before and after a site is removed, during the surgery.

Further, for example, the arm movement controlling function 344 is configured to obtain, as operation information, a moving amount of the medical tool based on the operation performed by the practitioner who operates the surgery assistance robot apparatus 2. In other words, the arm movement controlling function 344 obtains, as the operation information, moving amounts of the arm and the medical tool expected after the correcting process is applied to the operation performed by the practitioner on the operation interface 221 of the console 22 included in the surgery assistance robot apparatus 2.

Further, for example, the arm movement controlling function 344 judges whether or not the medical tool will be in contact with the surrounding site after the medical tool is moved. When having determined that the medical tool would be in contact with the surrounding site, the arm movement controlling function 344 controls motion of the surgery assistance robot apparatus 2 so as to avoid the contact of the medical tool with the surrounding site. In one example, when the operator performs an operation on the operation interface 221 to move the forceps 51 indicated in the three-dimensional model illustrated in FIG. 3, the arm movement controlling function 344 obtains the moving amount of the forceps 51 corresponding to the operation received by the operation interface 221.

Further, the arm movement controlling function 344 simulates in the three-dimensional model whether or not the forceps 51 will be in contact with the region R2 when being moved by the obtained moving amount. When having determined that the forceps 51 would be in contact with the region R2, the arm movement controlling function 344 controls the robot arm 21 so as to avoid the situation where the forceps 51 come into contact with the region R2. In other words, by transmitting a control signal to the surgery assistance robot apparatus 2, the arm movement controlling function 344 controls the motion of the robot arm 21.

In this situation, for example, the arm movement controlling function 344 is capable of controlling the arm so that the forceps 51 move up to the point just before coming into contact with the region R2 and is also capable of controlling the arm so that the forceps 51 do not move at all. Further, for example, the arm movement controlling function 344 is also capable of controlling the arm so that the forceps 51 move up to the point just before coming into contact with the region R2 and subsequently move in a direction different from the direction toward the region R2. Any of these types of control may arbitrarily be selected by the practitioner.

On the contrary, when having determined that the forceps 51 will not be in contact with the region R2, the arm movement controlling function 344 controls the arm so that the forceps 51 move by the moving amount corresponding to the operation received by the operation interface 221. Further, during the simulation, also when having determined that the forceps 51 will be in contact with the region R1 subject to the treatment, the arm movement controlling function 344 controls the arm so that the forceps 51 move by a moving amount corresponding to the operation received by the operation interface 221. In other words, when having determined that the medical tool would come into contact with a location other than the location subject to the treatment, the arm movement controlling function 344 exercises control to avoid situation where the medical tool comes into contact with the location other than the location subject to the treatment.

Further, for example, the arm movement controlling function 344 is configured to estimate the pressure to be applied when the medical tool comes in contact with the surrounding site. When having determined that the estimated pressure exceeds a predetermined threshold value, the arm movement controlling function 344 controls motion of the surgery assistance robot apparatus 2 so as to avoid the contact of the medical tool with the surrounding site. In one example, when the operator performs an operation on the operation interface 221 to move the forceps 51 indicated in the three-dimensional model in FIG. 3, the arm movement controlling function 344 obtains a moving amount of the forceps 51 corresponding to the operation received by the operation interface 221.

After that, the arm movement controlling function 344 judges whether or not the forceps 51 will come into contact with the region R2 when being moved by the obtained moving amount and also simulates, in the three-dimensional model, the pressure to be applied in the contact. In this situation, when having determined that the forceps 51 would come into contact with the region R2 and that the estimated pressure exceeds the predetermined threshold value, the arm movement controlling function 344 controls the robot arm 21 so as to avoid the situation where the forceps 51 come into contact with the region R2.

In this situation, for example, the arm movement controlling function 344 is capable of controlling the arm so that the forceps 51 move up to the point just before coming into contact with the region R2 and is also capable of controlling the arm so that the forceps 51 do not move at all. Further, for example, the arm movement controlling function 344 is also capable of controlling the arm so that the forceps 51 move up to the point just before coming into contact with the region R2 and subsequently move in a direction different from the direction toward the region R2. Further, for example, the arm movement controlling function 344 is capable of controlling the arm so that the contact is made, up to the point where the pressure to be applied in the contact does not exceed the predetermined threshold value. Any of these types of control may arbitrarily be selected by the practitioner. In this situation, the pressure is estimated by using any of existing methods, on the basis of information about the shape and the material of the medical tool, the site to be in contact, and the like.

On the contrary, when having determined that the forceps 51 will not come into contact with the region R2 or that the forceps 51 will be in contact with the region R2 but the estimated pressure does not exceed the predetermined threshold value, the arm movement controlling function 344 controls the arm so that the forceps 51 move by the moving amount corresponding to the operation received by the operation interface 221. Further, during the simulation, also when having determined that the forceps 51 will come into contact with the region R1 subject to the treatment, the arm movement controlling function 344 controls the arm so that the forceps 51 move by the moving amount corresponding to the operation received by the operation interface 221.

In this situation, the threshold value related to the pressure is set on the basis of one or both of the type of the medical tool and the state of the medical tool. For example, when the medical tool to be in contact is a pair of forceps used for severing a tissue, the threshold value is set to a small value. On the contrary, when the medical tool held by an arm is an ultrasound probe, the threshold value is set to a large value. When the operated medical tool is an ultrasound probe, the arm movement controlling function 344 does not exercise control to keep the ultrasound probe out of contact, but exercises control so that the ultrasound probe is always in contact.

Further, for example, when the medical tool to be in contact is an electric scalpel, the threshold value is set to a small value while the electric current is turned on, whereas the threshold value is set to a large value while the electric current is turned off. In this situation, the type of the medical tool may be identified on the basis of, for example, the arm holding the medical tool. For example, information keeping arms in correspondence with medical tools held thereby is stored in the memory 33. The arm movement controlling function 344 is configured to refer to the information stored in the memory 33 and to identify the type of the moved medical tool on the basis of the arm currently being operated by the practitioner. Further, the arm movement controlling function 344 is configured to obtain the electric power on/off state of the electric scalpel from the surgery assistance robot apparatus 2.

In the embodiment above, the example was explained in which the information about the positional relationship between the medical tool inside the subject's body and the surrounding site is obtained from the three-dimensional model; however, possible embodiments are not limited to this example. The positional relationship may be obtained from simple coordinate information. In that situation, the arm movement controlling function 344 is configured to obtain the positional relationship on the basis of feature points of the medical tool and the site inside the subject's body. In other words, the arm movement controlling function 344 is configured to obtain the information about the positional relationship between the medical tool inside the subject's body and the surrounding site, by reading the coordinate information being stored in the memory 33 and indicating a relative positional relationship between the medical tool inside the subject's body and the surrounding site of the medical tool.

Further, in the embodiment above, the example was explained in which the moving amount of the medical tool based on the operation performed by the practitioner who operates the surgery assistance robot apparatus 2 is used as the operation information; however, possible embodiments are not limited to this example. For instance, a treatment plan may be used as the operation information. In that situation, the arm movement controlling function 344 obtains the moving amount of the medical tool included in the treatment plan for the subject, as the operation information.

As explained above, the treatment plan made by the treatment planning function 343 includes the approach path (e.g., coordinate information in the passing) of the medical tool to the region subject to the treatment. For example, the arm movement controlling function 344 obtains the approach path included in the treatment plan as the operation information. Further, the arm movement controlling function 344 judges whether or not the medical tool will come into contact with the surrounding site when being moved along the approach path or whether or not the pressure to be applied in the contact will exceed the predetermined threshold value.

In this situation, as explained above, the surgery assistance robot controlling apparatus 3 is capable of controlling the motion of the robot arm 21 by using the treatment plan. Accordingly, the surgery assistance robot controlling apparatus 3 is capable of automatically operating the medical tool. In that situation, the arm movement controlling function 344 moves the medical tool along the approach path included in the treatment plan read from the memory 33. In this situation, as explained above, every time the three-dimensional model is corrected, the treatment plan is corrected. Consequently, the arm movement controlling function 344 is able to control the motion of the robot arm 21, by using the treatment plan that follows changes in the shape of the inside of the subject's body and in the positional arrangements of the sites.

In other words, the surgery assistance robot controlling apparatus 3 is able to automatically move the medical tool inside the subject's body, without the medical tool damaging the surrounding site. In this situation, for example, it is also acceptable to exercise control so as to correct the three-dimensional model and the treatment plan again when it is determined, during the automatic control, that the medical tool would come into contact with the surrounding site or that the pressure in the contact exceeds the threshold value. In other words, during the automatic control, when the arm movement controlling function 344 exercises control to avoid the contact or the like, the three-dimensional model constructing function 342 corrects the three-dimensional model, so that the treatment planning function 343 corrects the treatment plan by using the corrected three-dimensional model.

In this situation, the practitioner is able to select and arbitrarily switch between the automatic control of the robot arm 21 and the manual control by the practitioner. For example, for a manipulation in which the region subject to the treatment is in a location relatively easily approachable and for a manipulation at the stage preceding an approach to the region subject to the treatment, the practitioner may select the automatic control of the robot arm 21. In contrast, for example, for a manipulation in which the region subject to the treatment is in a location difficult to approach, as well as for a manipulation in which the region subject to the treatment is positioned adjacent to a blood vessel or to a location that should not be damaged, and for a manipulation in which the approaching procedure involves passing through the vicinity of a blood vessel or a location that should not be damaged, the practitioner may select the manual control for the robot arm 21.

In this situation, the arm movement controlling function 344 may set the automatic control and the manual control as a default according to the various conditions described above. In that situation, for example, the arm movement controlling function 344 determines which condition applies to the manipulation to be performed, on the basis of the arrangement state of the medical tool inside the subject's body and the organ in the three-dimensional model and the treatment plan and further automatically sets either the automatic control or the manual control according to a result of the judgment. In this situation, when the practitioner approves the control set by the arm movement controlling function 344, the manipulation will be performed under the control in the setting. When the practitioner does not approve the setting, the practitioner selects one from between the automatic control and the manual control.

Further, the arm movement controlling function 344 is also capable of automatically switching between the automatic control and the manual control on the basis of manipulation information. In that situation, the controlling function 341 is configured to further obtain the manipulation information for the subject. More specifically, the controlling function 341 is configured to obtain the manipulation information used for judging whether or not the manipulation to be performed on the subject is a manipulation having many clinical cases. In this situation, as information used for judging whether or not the manipulation is one having many clinical cases, for example, it is acceptable to use information indicating whether or not an insurance from a public medical insurance system is applicable. Manipulations to which an insurance from the public medical insurance system is applicable satisfy various requirements related to effectiveness and safety of the manipulations and are backed up with a certain number of past clinical cases. Further, manipulations to which an insurance from the public medical insurance system is applicable will have an increased number of clinical cases in the future. Accordingly, the controlling function 341 obtains the manipulation information indicating whether or not an insurance is applicable to the manipulation, as the manipulation information indicating whether or not the manipulation to be performed on the subject is a manipulation having many clinical cases.

In this situation, for example, regarding manipulations using a surgery assistance robot, an insurance is applicable to "thoracoscopic surgery on a malignant mediastinal tumor", "thoracoscopic surgery on a benign mediastinal tumor", "thoracoscopic surgery on a malignant lung tumor (lung lobe removal or a wider area than one lung lobe)", "thoracoscopic surgery on a malignant esophageal tumor", "thoracoscopic valvuloplasty", "laparoscopic gastrectomy", "laparoscopic stomach fundectomy", "laparoscopic total gastrectomy", "laparoscopic proctectomy/rectal amputation", "laparoscopic surgery on a malignant bladder tumor", "laparoscopic surgery on a malignant uterine tumor (cancer of the uterine body only)", and "laparoscopic vaginal panhysterectomy", and the like.

On the basis of the manipulation information obtained by the controlling function 341, the arm movement controlling function 344 judges whether or not an insurance is applicable to the manipulation to be performed on the subject. In this situation, when an insurance is applicable to specifics of the manipulation indicated in the manipulation information, the arm movement controlling function 344 controls motion of the robot arm 21 on the basis of the result of the estimation. When an insurance is not applicable to the specifics of the manipulation indicated in the manipulation information, the arm movement controlling function 344 controls the motion of the robot arm 21 in accordance with the operation information. In other words, when an insurance is applicable to the manipulation to be performed on the subject, the arm movement controlling function 344 exercises the automatic control on the robot arm 21. On the contrary, when an insurance is not applicable to the manipulation to be performed on the subject, the arm movement controlling function 344 exercises the manual control on the robot arm 21.

Further, for example, it is also possible to set, in advance, which of the two control methods is prioritized for each practitioner. For example, with practitioners having higher skills, the arm movement controlling function 344 automatically sets the manual control. On the contrary, with practitioners who are less experienced, the arm movement controlling function 344 automatically sets the automatic control. The memory 33 stores therein information indicating which of the control methods is prioritized between the manual control and the automatic control, in correspondence with an ID of each practitioner, for example. The arm movement controlling function 344 refers to the correspondence information stored in the memory 33 and sets one of the control methods selected from between the manual control and the automatic control, on the basis of the ID of the practitioner of the manipulation to be performed.

As explained above, when the arm movement controlling function 344 controls the robot arm 21, the controlling function 341 causes display information indicating the control state of the surgery assistance robot apparatus 2 to be displayed. More specifically, for the surgery assistance robot apparatus 2, the controlling function 341 transmits information indicating specifics of the control exercised on the robot arm 21, to the display controlling apparatus 23 of the surgery assistance robot apparatus 2, so that the specifics of the control are displayed on a display 222 of the console and/or the display of the display controlling apparatus 23.

FIG. 4 is a drawing illustrating examples of display control realized by the controlling function 341 according to the first embodiment. FIG. 4 illustrates a picture from an endoscope and an ultrasound image displayed in a real-time manner on the display 222 of the console and/or the display of the display controlling apparatus 23 during the surgery. For example, during the surgery, as illustrated in the top section of FIG. 4, the display controlling apparatus 23 is capable of causing the display 222 or the like to display a three-dimensional image I1 that can be viewed stereoscopically, a two-dimensional image I2, and an ultrasound image I3. The three-dimensional image I1 and the two-dimensional image I2 illustrated in the top section of FIG. 4 are pictures taken by the endoscope. For example, the three-dimensional image I1 is an image in which the picture taken by the endoscope can be viewed stereoscopically, so that the practitioner is able to gain a visual perspective as if he/she was observing the actual surgical region.

For example, by processing two pictures respectively acquired by two lenses of a camera provided in the endoscope, the display controlling apparatus 23 causes the display 222 or the like to display as the three-dimensional image I1 that can be viewed stereoscopically. In this situation, the display controlling apparatus 23 is capable of causing the three-dimensional image I1 to be displayed as being enlarged or reduced in size in accordance with operations performed by the practitioner. The practitioner is able to precisely grip, peel, or sever a tissue, by viewing the three-dimensional image I1 that is displayed on the display 222 and can be viewed stereoscopically.

Further, for example, the two-dimensional image I2 is an image in which the picture taken by the endoscope is two-dimensionally displayed or an image generated from three-dimensional medical image data acquired before the surgery. In one example, the display controlling apparatus 23 causes the display 222 or the like to display a picture taken by one of the cameras of the endoscope or a CT image of the region subject to the treatment taken by an X-ray CT apparatus before the surgery.

Further, the ultrasound image I3 is a real-time ultrasound image acquired during the surgery and, for example, includes the region subject to the treatment. In other words, the ultrasound image I3 renders the inside of the tissue that cannot be observed through the cameras provided in the endoscope. In this situation, as illustrated in the top section of FIG. 4, for example, an icon of a camera is appended to the ultrasound image I3. This icon indicates the position of the endoscope with respect to the ultrasound image. In other words, by learning the position of the icon with respect to the ultrasound image, the practitioner is able to understand the positional relationship between the image from the endoscope (e.g., the three-dimensional image I1) and the ultrasound image I3. Accordingly, the practitioner is able to perform the manipulation while understanding the region subject to the treatment in details, by observing the region subject to the treatment from the outside through the three-dimensional image I1 and also observing the state on the inside of the region subject to the treatment through the ultrasound image I3.

Although FIG. 4 illustrates the example in which the ultrasound image is displayed as the real-time image, possible embodiments are not limited to this example. It is also acceptable to display a CT image acquired in a real-time manner. In that situation, for example, an icon of a camera is appended to the CT image, so as to provide information about a positional relationship between an image from the endoscope and the CT image. Further, although FIG. 4 illustrates the example in which the three images are displayed, possible embodiments are not limited to this example. It is also acceptable to display two or fewer images or four or more images. Further, the display controlling apparatus 23 is also capable of causing the display 222 or the like to display not only images but also vital signs obtained from the subject during the surgery, for example.

As explained above, the display controlling apparatus 23 causes the display 222 or the like to display the various types of information. In addition to the various types of information, the controlling function 341 is also capable of exercising control so that the display controlling apparatus 23 displays information indicating specifics of the control exercised on the robot arm 21. For example, when the arm movement controlling function 344 exercises control so that the medical tool will not come into contact with the surrounding site, the controlling function 341 causes information such as "! ADVANCEMENT INTO DANGEROUS REGION IS RESTRICTED" to be displayed in the three-dimensional image I1, as illustrated in the bottom section of FIG. 4.

With this arrangement, the practitioner is able to understand the control state and is thus able to safely perform the manipulation without damaging the surrounding site, by operating the operation interface 221 so that the advancement will not be restricted. As illustrated in the bottom section of FIG. 4, the controlling function 341 is also capable of causing a dangerous region R3 where contact should be avoided to be displayed while being superimposed on the display image. For example, the controlling function 341 is capable of specifying the position of the surrounding site within the image from the endoscope on the basis of the three-dimensional model set with the surrounding site and further causing the dangerous region to be displayed in color while being superimposed in the specified position.

Processing functions of the processing circuitry 34 included in the surgery assistance robot controlling apparatus 3 have thus been explained. In this situation, when the processing circuitry 34 is realized by using a processor, the processing functions of the processing circuitry 34 are stored in the memory 33 in the form of computer-executable programs. Further, the processing circuitry 34 is configured to realize the functions corresponding to the programs, by reading and executing the programs from the memory 33. In other words, the processing circuitry 34 that has read the programs has the functions illustrated within the processing circuitry 34 in FIG. 2. Further, although FIG. 2 illustrates the example in which the processing functions are realized by the single processor, another arrangement is also acceptable in which a processing circuit is structured by combining together a plurality of independent processors, so that the functions are realized as a result of the processors executing the programs. Further, the processing functions of the processing circuitry 34 may be realized as being distributed among, or integrated together in, one or more processing circuits, as appropriate. Further, although FIG. 2 illustrates the example in which the single memory (i.e., the memory 33) stores therein the programs corresponding to the processing functions, it is also acceptable to arrange a plurality of memories in a distributed manner, so that the processing circuitry reads a corresponding program from each of the individual memories.

Figure 5:
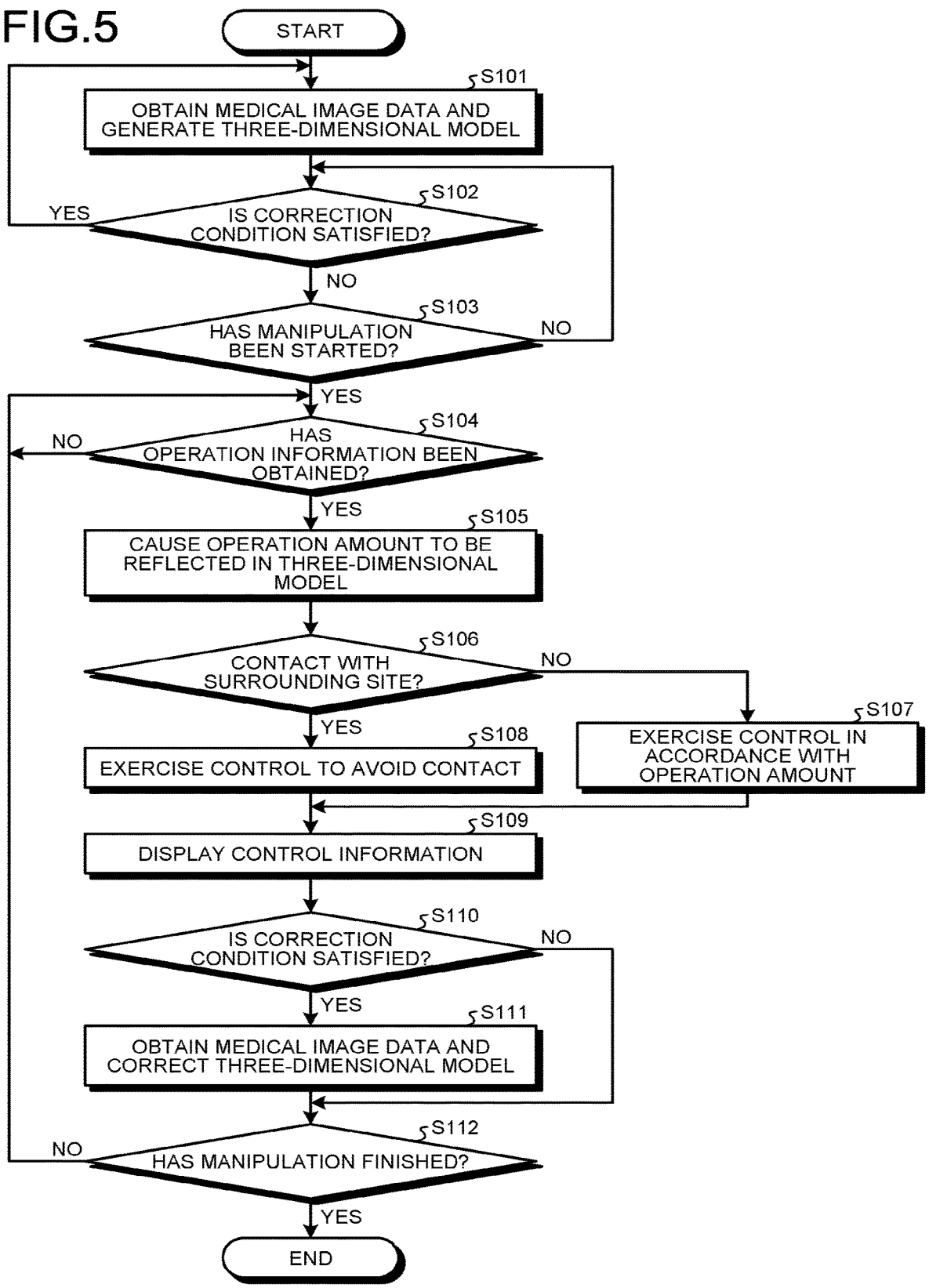
FIG. 5 is a flowchart illustrating a processing procedure performed by the surgery assistance robot controlling apparatus according to the first embodiment.
Figure 6:
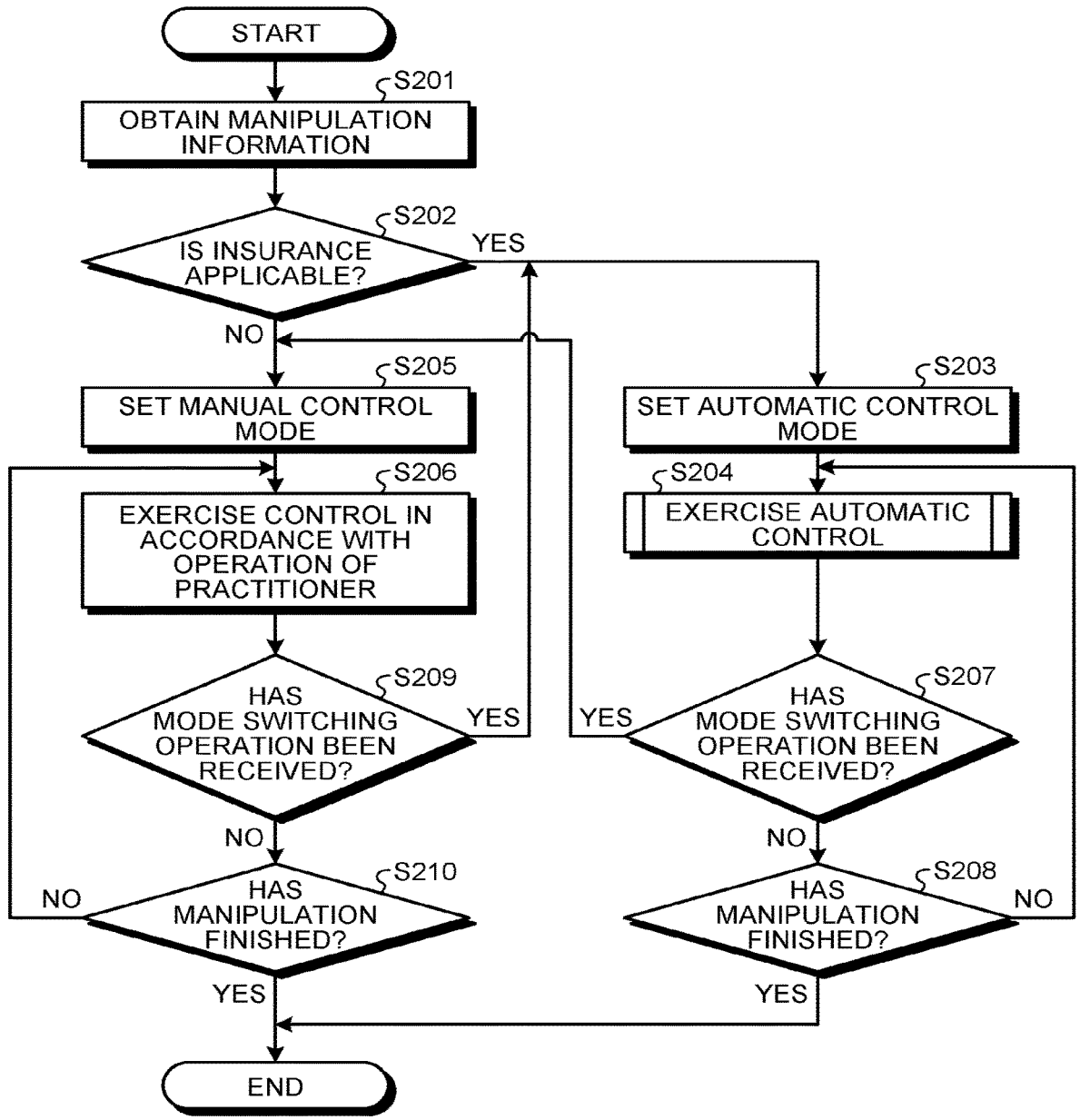
FIG. 6 is a flowchart illustrating another processing procedure performed by the surgery assistance robot controlling apparatus according to the first embodiment.

Next, processing procedures performed by the surgery assistance robot controlling apparatus 3 will be explained, with reference to FIGS. 5 and 6. FIGS. 5 and 6 are flowcharts illustrating the processing procedures performed by the surgery assistance robot controlling apparatus 3 according to the first embodiment. FIG. 5 illustrates a process related to the automatic control of the robot arm 21. Further, FIG. 5 illustrates an example in which the three-dimensional model is obtained as the positional relationship, and operations performed by the practitioner are obtained as the operation information. Further, FIG. 5 illustrates the process in which the judgment is made as to whether or not the medical tool will come into contact with the surrounding site. Further, FIG. 5 illustrates details of the process at step S204 in FIG. 6. FIG. 6 illustrates a process related to switching between the automatic control and the manual control of the robot arm 21.

Steps S101, S102, S110, and S111 in FIG. 5 are steps realized as a result of the processing circuitry 34 invoking and executing the program corresponding to the three-dimensional model constructing function 342 from the memory 33. Steps S103, S109, and S112 in FIG. 5 are steps realized as a result of the processing circuitry 34 invoking and executing the program corresponding to the controlling function 341 from the memory 33. Steps S104 through S108 in FIG. 5 are steps realized as a result of the processing circuitry 34 invoking and executing the program corresponding to the arm movement controlling function 344 from the memory 33.

As illustrated in FIG. 5, in the surgery assistance robot controlling apparatus 3, the processing circuitry 34 at first obtains medical image data and generates a three-dimensional model (step S101). Further, the processing circuitry judges whether or not the correction condition is satisfied (step S102). When the correction condition is satisfied (step S102: Yes) the processing circuitry 34 returns to step S101 and generates a three-dimensional model. On the contrary, when the correction condition is not satisfied (step S102: No), the processing circuitry 34 judges whether or not a manipulation has been started (step S103). Until a manipulation is started (step S103: No), the processing circuitry 34 continues the judging process at step S102.

On the contrary, when a manipulation has been started (step S103: Yes), the processing circuitry 34 judges whether or not the operation information has been obtained (step S104). Until the operation information is obtained (step S104: No), the processing circuitry 34 is in a standby state. On the contrary, when the operation information has been obtained (step S104: Yes), the processing circuitry 34 causes the operation amount to be reflected in the three-dimensional model (step S105) and judges whether or not the medical tool will come into contact with the surrounding site (step S106).

When the medical tool will not come into contact with the surrounding site (step S106: No), the processing circuitry 34 exercises control in accordance with the operation amount (step S107). On the contrary, when the medical tool would come into contact with the surrounding site (step S106: Yes), the processing circuitry 34 exercises control so as to avoid the contact (step S108) and causes the control information to be displayed (step S109).

Subsequently, the processing circuitry 34 judges whether or not the correction condition is satisfied (step S110). When the correction condition is satisfied (step S110: Yes), the processing circuitry 34 obtains the medical image data and corrects the three-dimensional model (step S111) and judges whether or not the manipulation has finished (step S112). On the contrary, when the correction condition is not satisfied (step S110: No), the processing circuitry 34 proceeds to step S112 and judges whether or not the manipulation has finished.

At step S112, when the manipulation has not finished (step S112: No), the processing circuitry 34 returns to step S104 and judges whether or not the operation information has been obtained. On the contrary, when the manipulation has finished (step S112: Yes), the processing circuitry 34 ends the process.

Step at S201 in FIG. 6 is a step realized as a result of the processing circuitry 34 invoking and executing the program corresponding to the controlling function 341 from the memory 33. Steps S202 through S210 in FIG. 6 are steps realized as a result of the processing circuitry 34 invoking and executing the program corresponding to the arm movement controlling function 344 from the memory 33.

As illustrated in FIG. 6, in the surgery assistance robot controlling apparatus 3, the processing circuitry 34 at first obtains the manipulation information (step S201) and judges whether or not an insurance is applicable (step S202). In this situation, when an insurance is applicable (step S202: Yes), the processing circuitry 34 sets the automatic control mode (step S203) and exercises the automatic control (step S204).

On the contrary, when an insurance is not applicable (step S202: No), the processing circuitry 34 sets the manual control mode (step S205) and exercises control in accordance with operations performed by the practitioner (step S206). Further, the processing circuitry 34 judges whether or not a mode switching operation is received during the control.

For example, the processing circuitry 34 judges whether or not a mode switching operation is received while the automatic control is being exercised (step S207). When a mode switching operation is received (step S207: Yes), the processing circuitry 34 sets the manual control mode (step S205) and continues the process. On the contrary, when no mode switching operation is received (step S207: No), the processing circuitry 34 judges whether or not the manipulation has finished (step S208). When the manipulation has finished (step S208: Yes), the processing circuitry 34 ends the process. On the contrary, when the manipulation has not finished (step S208: No), the processing circuitry 34 continues to exercise the automatic control (step S204).

In another example, the processing circuitry 34 judges whether or not a mode switching operation is received while the manual control is being exercised (step S209). When a mode switching operation is received (step S209: Yes), the processing circuitry 34 sets the automatic control mode (step S203) and continues the process. On the contrary, when no mode switching operation is received (step S209: No), the processing circuitry 34 judges whether or not the manipulation has finished (step S210). When the manipulation has finished (step S210: Yes), the processing circuitry 34 ends the process. On the contrary, when the manipulation has not finished (step S210: No), the processing circuitry 34 continues to exercise the manual control (step S206).

As explained above, according to the first embodiment, the controlling function 341 is configured to obtain the operation information used for putting the surgery assistance robot apparatus 2 into the motion, the surgery assistance robot apparatus 2 holding the medical tool to be inserted into the subject's body and being configured to move the medical tool. On the basis of the positional relationship between the medical tool inside subject's body and the surrounding site, as well as the operation information, the arm movement controlling function 344 is configured to estimate the position of the medical tool with respect to the surrounding site expected after the medical tool is moved and to control the motion of the surgery assistance robot apparatus 2 on the basis of the result of the estimation. Accordingly, the surgery assistance robot controlling apparatus 3 according to the first embodiment is able to control the robot arm 21 by estimating the positional relationship between the medical tool and the surrounding site expected when the operation is performed. It is therefore possible to improve safety of the manipulation using the surgery assistance robot apparatus.

As a result, the surgery assistance robot controlling apparatus 3 makes it possible to perform the manipulation by using the surgery assistance robot apparatus regardless of the skills of the practitioner. It is therefore possible to promote introducing the manipulations that use the surgery assistance robot apparatus. Further, as a result of promoting introducing the manipulations, a larger number of people will be able to receive less invasive treatment. It is therefore possible to contribute to enhancement of Quality Of Life (QOL) of subjects.

Further, according to the first embodiment, the arm movement controlling function 344 is configured to estimate the contact state between the surrounding site and the medical tool expected after the medical tool is moved and to control the motion of the surgery assistance robot on the basis of the result of the estimation. Consequently, the surgery assistance robot controlling apparatus 3 according to the first embodiment makes it possible to change the control exercised on the robot arm 21, depending on the contact state between the medical tool and the surrounding site.

Further, according to the first embodiment, the arm movement controlling function 344 is configured to judge whether or not the medical tool will come into contact with the surrounding site after the medical tool is moved. When having determined that the medical tool would come into contact with the surrounding site, the arm movement controlling function 344 is configured to control the motion of the surgery assistance robot apparatus 2 so as to avoid the contact of the medical tool with the surrounding site. Consequently, the surgery assistance robot controlling apparatus 3 according to the first embodiment makes it possible to avoid the contact between the medical tool and the surrounding site.

Further, according to the first embodiment, the arm movement controlling function 344 is configured to estimate the pressure to be applied when the medical tool comes into contact with the surrounding site. When having determined that the estimated pressure exceeds the predetermined threshold value, the arm movement controlling function 344 is configured to control the motion of the surgery assistance robot apparatus 2 so as to avoid the contact of the medical tool with the surrounding site. Consequently, the surgery assistance robot controlling apparatus 3 according to the first embodiment makes it possible to change the control exercised on the robot arm 21 in accordance with the degree of the contact between the medical tool and the surrounding site.

Further, according to the first embodiment, the predetermined threshold value is set on the basis of one or both of the type of the medical tool and the state of the medical tool. Consequently, the surgery assistance robot controlling apparatus 3 according to the first embodiment makes it possible to change the degree of contact used in the judging process, depending on situations.

Further, according to the first embodiment, the three-dimensional model constructing function 342 is configured to generate the three-dimensional model, on the basis of the medical image data acquired from the subject and the data related to the medical tool. Further, the arm movement controlling function 344 is configured to obtain the positional relationship on the basis of the three-dimensional model indicating the medical tool and the site inside the subject's body. Consequently, the surgery assistance robot controlling apparatus 3 according to the first embodiment makes it possible to understand an accurate positional relationship between the medical tool and the surrounding site.

Further, according to the first embodiment, the arm movement controlling function 344 is configured to obtain the positional relationship on the basis of the feature points of the medical tool and the site in the subject's body. Consequently, the surgery assistance robot controlling apparatus 3 according to the first embodiment makes it possible to omit the process of generating the three-dimensional model.

Further, according to the first embodiment, the arm movement controlling function 344 is configured to obtain the positional relationship at least at each of the times when the posture of the subject is fixed, when a space is formed in the abdominal cavity, and before and after a site is removed, during the surgery. Consequently, the surgery assistance robot controlling apparatus 3 according to the first embodiment makes it possible to address the changes of the shapes and the positional arrangements inside the abdominal cavity.

Further, according to the first embodiment, the controlling function 341 is configured to obtain, as the operation information, the moving amount of the medical tool based on the operation performed by the practitioner who operates the surgery assistance robot apparatus 2. Consequently, the surgery assistance robot controlling apparatus 3 according to the first embodiment makes it possible to make judgments by using the accurate moving amount.

Further, according to the first embodiment, the controlling function 341 is configured to obtain, as the operation information, the moving amount of the medical tool included in the treatment plan for the subject. Consequently, the surgery assistance robot controlling apparatus 3 according to the first embodiment makes the automatic control of the surgery assistance robot apparatus 2 possible.

Further, according to the first embodiment, the treatment planning function 343 is configured to correct the treatment plan when the motion of the surgery assistance robot is controlled so as to avoid the contact of the medical tool with the surrounding site. Consequently, the surgery assistance robot controlling apparatus 3 according to the first embodiment makes it possible to exercise the automatic control on the surgery assistance robot apparatus 2 more safely.

Further, according to the first embodiment, the controlling function 341 is configured to cause the display information indicating the control state of the surgery assistance robot apparatus 2 to be displayed. Consequently, the surgery assistance robot controlling apparatus 3 according to the first embodiment makes it possible for the practitioner to understand the control state.

Further, according to the first embodiment, the controlling function 341 is configured to further obtain the manipulation information for the subject. When an insurance is applicable to the specifics of the manipulation indicated in the manipulation information, the arm movement controlling function 344 is configured to control the motion of the surgery assistance robot on the basis of the result of the estimation. When an insurance is not applicable to the specifics of the manipulation indicated in the manipulation information, the arm movement controlling function 344 is configured to control the motion of the surgery assistance robot in accordance with the operation information. Consequently, the surgery assistance robot controlling apparatus 3 according to the first embodiment is able to automatically switch between the automatic control and the manual control in accordance with the number of clinical cases and thus makes it possible to efficiently reduce burdens imposed on the practitioner.

Second Embodiment

The first embodiment has thus been explained. It is, however, possible to carry out the present disclosure in various different modes other than those described in the first embodiment above.

In the embodiments above, the example was explained in which the surgery assistance robot controlling apparatus 3 performs the processes; however, possible embodiments are not limited to this example. For instance, the processes may be performed by the medical image diagnosis apparatus 1 or the surgery assistance robot apparatus 2. In those situations, for example, a memory included in the medical image diagnosis apparatus 1 stores therein the programs corresponding to the controlling function 341, the three-dimensional model constructing function 342, the treatment planning function 343, and the arm movement controlling function 344. Further, a processing circuitry included in the medical image diagnosis apparatus 1 is configured to perform the same processes as those described above, by reading and executing the programs corresponding to the controlling function 341, the three-dimensional model constructing function 342, the treatment planning function 343, and the arm movement controlling function 344 from the memory. The processing circuitry is realized by using a processor, for example.

In another example, a memory included in the surgery assistance robot apparatus 2 stores therein the programs corresponding to the controlling function 341, the three-dimensional model constructing function 342, the treatment planning function 343, and the arm movement controlling function 344. Further, a processing circuitry included in the surgery assistance robot apparatus 2 is configured to perform the same processes as those described above, by reading and executing the programs corresponding to the controlling function 341, the three-dimensional model constructing function 342, the treatment planning function 343, and the arm movement controlling function 344 from the memory. The processing circuitry is realized by using a processor, for example.

Further, the processes described above may be executed by the medical image diagnosis apparatus 1 and the surgery assistance robot apparatus 2 in a distributed manner. In that situation, for example, a memory included in the medical image diagnosis apparatus 1 stores therein the programs corresponding to the controlling function 341, the three-dimensional model constructing function 342, and the treatment planning function 343. Further, processing circuitry included in the medical image diagnosis apparatus 1 is configured to perform the processes related to the generation of the three-dimensional model and the treatment plan described above, by reading and executing the programs corresponding to the controlling function 341, the three-dimensional model constructing function 342, and the treatment planning function 343 from the memory.

Further, a memory included in the surgery assistance robot apparatus 2 stores therein the programs corresponding to the controlling function 341 and the arm movement controlling function 344. Further, processing circuitry included in the surgery assistance robot apparatus 2 is configured to perform the judging process and the arm controlling process described above, by reading and executing the programs corresponding to the controlling function 341 and the arm movement controlling function 344 from the memory.

Further, the distribution described above is merely an example. The functions may be executed while being distributed arbitrarily.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in the memory 33. In this situation, instead of saving the programs in the memory 33, it is also acceptable to directly incorporate the programs in the circuits of the processors. In that situation, the processors realize the functions by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

In this situation, the programs (the controlling program) executed by the one or more processors are provided as being incorporated in advance in a Read-Only Memory (ROM), a storage circuitry, or the like. Further, the programs may be provided as being recorded on a computer-readable storage medium such as a Compact Disk (CD)-ROM, a Flexible Disk (FD), a Compact Disk Recordable (CD-R), a Digital Versatile Disk (DVD), or the like, in a file that is in an installable or executable format for the devices. Further, the programs may be saved in a computer connected to a network such as the Internet so as to be provided or distributed as being downloaded via the network. For example, the programs are structured as modules including the functional units described above. In actual hardware, as a result of a CPU reading and executing the programs from a storage medium such as a ROM, the modules are loaded into a main storage device so as to be generated in the main storage device.

According to at least one aspect of the embodiments described above, it is possible to improve safety of the manipulations using the surgery assistance robot device.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
processing circuitry configured to
obtain operation information used for putting a surgery assistance robot into motion, the surgery assistance robot holding a medical tool to be inserted into a body of a subject and being configured to move the medical tool with a moving amount based on an operation amount of an operation interface actually operated by a practitioner who operates the surgery assistant robot, the operation information resulting from a correction process, including a process of correcting unstable hand movements, applied to the operation amount of the operation interface actually operated by the practitioner; and
estimate a contact state between the medical tool and a surrounding site expected after the medical tool is moved by a moving amount based on the obtained operation amount of the operation interface, based on a positional relationship between the medical tool inside the body of the subject and the surrounding site, as well as the operation information, the moving amount being information that converts the operation amount of the operation interface into a movement of the medical tool, wherein the processing circuitry is further configured to
when having determined that the medical tool would come into contact with the surrounding site, restrict the motion of the surgery assistance robot so as to avoid the contact of the medical tool with the surrounding site, and cause display information indicating a restricted state of the surgery assistance robot on a medical image of the surrounding site to be displayed.

2. The medical image diagnosis apparatus according to claim 1, wherein the processing circuitry is further configured to:
estimate pressure to be applied if the medical tool would come into contact with the surrounding site, and
when having determined that the estimated pressure exceeds a predetermined threshold value, restrict the motion of the surgery assistance robot so as to avoid the contact of the medical tool with the surrounding site.

3. The medical image diagnosis apparatus according to claim 2, wherein the predetermined threshold value is set based on one or both of a type of the medical tool and a state of the medical tool.

4. The medical image diagnosis apparatus according to claim 1, wherein the processing circuitry is further configured to obtain the positional relationship based on a three-dimensional model indicating the medical tool and a site inside the body of the subject.

5. The medical image diagnosis apparatus according to claim 4, wherein the processing circuitry is further configured to generate the three-dimensional model based on medical image data acquired from the subject and data related to the medical tool.

6. The medical image diagnosis apparatus according to claim 1, wherein the processing circuitry is further configured to obtain the positional relationship based on the medical tool and feature points of a site inside the body of the subject.

7. The medical image diagnosis apparatus according to claim 1, wherein the processing circuitry is further configured to obtain the positional relationship at least at each of times when a posture of the subject is fixed, when a space is formed in an abdominal cavity, and before and after a site is removed, during surgery.

8. The medical image diagnosis apparatus according to claim 1, wherein, as the operation information, the processing circuitry is further configured to obtain the moving amount of the medical tool included in a treatment plan for the subject.

9. The medical image diagnosis apparatus according to claim 8, wherein the processing circuitry is further configured to correct the treatment plan, when restricting the motion of the surgery assistance robot so as to avoid contact of the medical tool with the surrounding site.

10. The medical image diagnosis apparatus according to claim 1, wherein the processing circuitry is further configured to
obtain manipulation information for the subject,
determine whether or not the manipulation to be performed on the subject is a manipulation having many clinical cases,
when determining that the manipulation to be performed on the subject is a manipulation having many clinical cases, control the motion of the surgery assistance robot based on the result of the estimation, and
when determining that the manipulation to be performed on the subject is not a manipulation having many clinical cases, restrict the motion of the surgery assistance robot by manual control in accordance with the operation information.

11. A surgery assistance robot apparatus, comprising:
an arm configured to hold a medical tool to be inserted into a body of a subject and to move the medical tool with a moving amount resulting from a correction process, including a process of correcting unstable hand movements, applied to an operation amount of an operation interface actually operated by a practitioner who operates the surgery assistance robot; and
processing circuitry configured to
estimate a contact state between the medical tool and a surrounding site expected after the medical tool is moved by a moving amount based on the operation amount of the operation interface, based on a positional relationship between the medical tool inside the body of the subject and the surrounding site as well as the operation amount of the operation interface, the moving amount being information that converts the operation amount of the operation interface into a movement of the medical tool, wherein
the processing circuitry is further configured to, when having determined that the medical tool would come into contact with the surrounding site, restrict the motion of the arm so as to avoid the contact of the medical tool with the surrounding site, and cause display information indicating a restricted state of the surgery assistance robot on a medical image of the surrounding site to be displayed.

12. A surgery assistance robot controlling apparatus, comprising:
processing circuitry configured to
obtain operation information used for putting a surgery assistance robot into motion, the surgery assistance robot holding a medical tool to be inserted into a body of a subject and being configured to move the medical tool with a moving amount based on an operation amount of an operation interface actually operated by a practitioner who operates the surgery assistance robot, the operation information resulting from a correction process, including a process of correcting unstable hand movements, applied to the operation amount of the operation interface actually operated by the practitioner; and estimate a contact state between the medical tool and a surrounding site expected after the medical tool is moved by a moving amount based on the obtained operation amount of the operation interface, based on a positional relationship between the medical tool inside the body of the subject and the surrounding site as well as the operation information, the moving amount being information that converts the operation amount of the operation interface into a movement of the medical tool, wherein the processing circuitry is further configured to when having determined that the medical tool would come into contact with the surrounding site, restrict the motion of the surgery assistance robot so as to avoid the contact of the medical tool with the surrounding site, and cause display information indicating a restricted state of the surgery assistance robot on a medical image of the surrounding site to be displayed.

13. A controlling method, comprising:

obtaining operation information used for putting a surgery assistance robot into motion, the surgery assistance robot holding a medical tool to be inserted into a body of a subject and being configured to move the medical tool with a moving amount based on an operation amount of an operation interface actually operated by a practitioner who operates the surgery assistance robot, the operation information resulting from a correction process, including a process of correcting unstable hand movements, applied to the operation amount of the operation interface actually operated by the practitioner;

estimating a contact state between the medical tool and a surrounding site expected after the medical tool is moved by a moving amount based on the obtained operation amount of the operation interface, based on a positional relationship between the medical tool inside the body of the subject and the surrounding site as well as the operation information, the moving amount being information that converts the operation amount of the operation interface into a movement of the medical tool; and when having determined that the medical tool would come into contact with the surrounding site, restricting the motion of the surgery assistance robot so as to avoid the contact of the medical tool with the surrounding site, and causing display information indicating a restricted state of the surgery assistance robot on a medical image of the surrounding site to be displayed.

* * * * *